United States Patent [19]
Lochrie et al.

[11] Patent Number: 5,726,017
[45] Date of Patent: Mar. 10, 1998

[54] HIGH AFFINITY HIV-1 GAG NUCLEIC ACID LIGANDS

[75] Inventors: Michael A. Lochrie; Larry Gold, both of Boulder, Colo.

[73] Assignee: NeXstar Pharmaceuticals, Inc., Boulder, Colo.

[21] Appl. No.: 447,172

[22] Filed: May 19, 1995

Related U.S. Application Data

[63] Continuation-in-part of Ser. No. 714,131, Jun. 10, 1991, Pat. No. 5,475,096, said Ser. No. 931,473, Aug. 17, 1992, Pat. No. 5,270,163, said Ser. No. 964,624, Oct. 21, 1992, Pat. No. 5,496,938, said Ser. No. 117,991, Sep. 8, 1993, abandoned, and Ser. No. 536,428, Jun. 11, 1990, abandoned.

[51] Int. Cl.$^6$ .................... C12Q 1/68; C12P 19/34; C07H 21/04; C07H 21/02
[52] U.S. Cl. .................. 435/6; 435/91.2; 536/23.1; 536/25.4; 935/77; 935/78
[58] Field of Search ................ 435/6, 91.2; 536/23.1, 536/25.4

[56] References Cited

U.S. PATENT DOCUMENTS 5,496,938  3/1996  Gold et al. .................. 435/6

FOREIGN PATENT DOCUMENTS 2 183 661 A  6/1987  United Kingdom .
WO 89/06694  7/1989  WIPO .

OTHER PUBLICATIONS

Anderson (1994) Human Gene Therapy 5:149.
Berkowitz et al. (1993) J. Virology 67:7190.
Buchschacher, Jr. (1993) JAMA 269:2880.
Clever et al. (1995) J. Virology 69:2101.
Joshi et al. (1991) J. Virology 65:5524.
Luban and Goff (1991) J. Virology 65:3203.
Niedrig et al. (1994) J. Virology 75:1469.
Rice et al. (1993) Proc. Natl. Acad. Sci. USA 90:9721.
Tanchou et al. (1994) Aids Research and Human Retroviruses 10:983.
Joyce (1989) Gene 82:83.
Joyce and Inoue (1989) Neucleic Acids Research 17:711.
Ellington and Szostak (1990) Abstract of papers presented at the 1990 meeting on RNA Processing, Cold Spring harbor laboratory, Cold Spring harbor, NY, p. 226.
Kinzler and Vogelstein (1989) Nucleic Acids Research 17:3645.
Kramer et al. (1974) J. Mol. Biol. 89–719.
Levisohn and Spiegelman (1969) Proc. Natl. Acad. Sci. USA 63:805.
Levisohn and Spiegelman (1968) Proc. Natl. Acad. Sci. USA 60:866.
Oliphant et al (1989) Mol. Cell Biol. 9:2944.
Oliphant and Struhl (1988) Nucleic Acids Research 16:7673.
Oliphant and Struhl (1987) Methods in Enzymology 155:568.
Oliphant et al. (1986) Gene 44:177.
Robertson and Joyce (1990) Nature 344:467.
Thiesen and Bach (1990) Nucleic Acids Research 18:3203.
Gura, Science 270:575–577 (27 Oct. 1995).
Hobbs et al., 1973.

*Primary Examiner*—Stephanie W. Zitomer
*Attorney, Agent, or Firm*—Swanson & Bratschun LLC

[57] ABSTRACT

Methods are described for the identification and preparation of high-affinity nucleic acid ligands to HIV-1 GAG. Included in the invention are specific RNA ligands to HIV-1 GAG identified by the SELEX method. Also included are RNA ligands that inhibit the function of HIV-1 GAG.

10 Claims, No Drawings

SEQUENCE LISTING ( 1 ) GENERAL INFORMATION:

( i i i ) NUMBER OF SEQUENCES: 47

( 2 ) INFORMATION FOR SEQ ID NO:1:

( i ) SEQUENCE CHARACTERISTICS:
        ( A ) LENGTH: 97 base pairs (B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:1:

GGGAGACAAG AATAAACGCT CAANNNNNNN NNNNNNNNNN NNNNNNNNNN 50

NNNNNNNNNN NNNNNNNNNN NNNTTCGACA GGAGGCTCAC AACAGGC 97

(2) INFORMATION FOR SEQ ID NO:2:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:2:

TAATACGACT CACTATAGGG AGACAAGAAT AAACGCTCAA 40

(2) INFORMATION FOR SEQ ID NO:3:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:3:

GCCTGTTGTG AGCCTCCTGT CGAA 24

(2) INFORMATION FOR SEQ ID NO:4:

(i) SEQUENCE CHARACTERISTICS:
(A) LENGTH: 97 base pairs
(B) TYPE: nucleic acid
(C) STRANDEDNESS: single
(D) TOPOLOGY: linear (ii) MOLECULE TYPE: RNA (xi) SEQUENCE DESCRIPTION: SEQ ID NO:4:

GGGAGACAAG AAUAAACGCU CAANNNNNNN NNNNNNNNNN NNNNNNNNNN 50

NNNNNNNNNN NNNNNNNNNN NNNUUCGACA GGAGGCUCAC AACAGGC 97

(2) INFORMATION FOR SEQ ID NO:5:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:5:

GCCGGATCCG CCTGTTGTGA GCCTCCTGTC GAA 33

(2) INFORMATION FOR SEQ ID NO:6:

(i) SEQUENCE CHARACTERISTICS:
(A) LENGTH: 48 base pairs
(B) TYPE: nucleic acid ( C ) STRANDEDNESS: single
        ( D ) TOPOLOGY: linear ( i i ) MOLECULE TYPE: DNA ( x i ) SEQUENCE DESCRIPTION: SEQ ID NO:6:

CCGAAGCTTA ATACGACTCA CTATAGGGAG ACAAGAATAA ACGCTCAA 48

( 2 ) INFORMATION FOR SEQ ID NO:7:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

TAATACGACT CACTATA 17

( 2 ) INFORMATION FOR SEQ ID NO:8:

( i ) SEQUENCE CHARACTERISTICS:
        ( A ) LENGTH: 97 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:8:

GGGAGACAAG AAUAAACGCU CAAUUGUGAU CUACCGUUAC CUGACGGACG 50

UGUUUUUACA CCAACGAACC UGGUUCGACA GGAGGCUCAC AACAGGC 97

( 2 ) INFORMATION FOR SEQ ID NO:9:

( i ) SEQUENCE CHARACTERISTICS:
        ( A ) LENGTH: 97 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:9:

GGGAGACAAG AAUAAACGCU CAAUGAACCU CUGAGUUCUU CAUAGAACUG 50

AUAUCUUCAA GAAGGGGUAG AUGUUCGACA GGAGGCUCAC AACAGGC 97

( 2 ) INFORMATION FOR SEQ ID NO:10:

( i ) SEQUENCE CHARACTERISTICS:
        ( A ) LENGTH: 97 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:10:

GGGAGACAAG AAUAAACGCU CAACGUCUUC UACAGGGAAC CGUGGUGCAU 50

CUGUGAAGUU GUAGAUUCCU AGUUUCGACA GGAGGCUCAC AACAGGC 97

( 2 ) INFORMATION FOR SEQ ID NO:11:

( i ) SEQUENCE CHARACTERISTICS:
        ( A ) LENGTH: 97 base pairs ( B ) TYPE: nucleic acid
( C ) STRANDEDNESS: single
( D ) TOPOLOGY: linear ( i i ) MOLECULE TYPE: RNA ( x i ) SEQUENCE DESCRIPTION: SEQ ID NO:11:

```
GGGAGACAAG AAUAAACGCU CAAGGGUUGA UUACCAAAUC GUAACCUGUA   50
CCCUGCCUAC ACUAGGACAA CGGUUCGACA GGAGGCUCAC AACAGGC      97
```

( 2 ) INFORMATION FOR SEQ ID NO:12:

( i ) SEQUENCE CHARACTERISTICS:
( A ) LENGTH: 97 base pairs
( B ) TYPE: nucleic acid
( C ) STRANDEDNESS: single
( D ) TOPOLOGY: linear ( i i ) MOLECULE TYPE: RNA ( x i ) SEQUENCE DESCRIPTION: SEQ ID NO:12:

```
GGGAGACAAG AAUAAACGCU CAACUAACCG AAGCUCUGAG AAAUAGUUUA   50
UCCAGUGAAU GAAUCCUGAU GGGUUCGACA GGAGGCUCAC AACAGGC      97
```

( 2 ) INFORMATION FOR SEQ ID NO:13:

( i ) SEQUENCE CHARACTERISTICS:
( A ) LENGTH: 97 base pairs
( B ) TYPE: nucleic acid
( C ) STRANDEDNESS: single
( D ) TOPOLOGY: linear ( i i ) MOLECULE TYPE: RNA ( x i ) SEQUENCE DESCRIPTION: SEQ ID NO:13:

```
GGGAGACAAG AAUAAACGCU CAACGAGCUU UUAGUAAGAC UCAUGCCGAG   50
AAAUCGGUCG UGAUGCUGUC GAGUUCGACA GGAGGCUCAC AACAGGC      97
```

( 2 ) INFORMATION FOR SEQ ID NO:14:

( i ) SEQUENCE CHARACTERISTICS:
( A ) LENGTH: 97 base pairs
( B ) TYPE: nucleic acid
( C ) STRANDEDNESS: single
( D ) TOPOLOGY: linear ( i i ) MOLECULE TYPE: RNA ( x i ) SEQUENCE DESCRIPTION: SEQ ID NO:14:

```
GGGAGACAAG AAUAAACGCU CAAGCCCGGG AAUUGCAUGU UGUGCGUGCC   50
GGGAGUCCAA GUCAGCAUCC UCAUUCGACA GGAGGCUCAC AACAGGC      97
```

( 2 ) INFORMATION FOR SEQ ID NO:15:

( i ) SEQUENCE CHARACTERISTICS:
( A ) LENGTH: 97 base pairs
( B ) TYPE: nucleic acid
( C ) STRANDEDNESS: single
( D ) TOPOLOGY: linear ( i i ) MOLECULE TYPE: RNA ( x i ) SEQUENCE DESCRIPTION: SEQ ID NO:15:

```
GGGAGACAAG AAUAAACGCU CAAGGGUUGA UUACCAAAUC GUAACCUGUA   50
CCCUGCCUAC CCUAGGACAA CGAUUCGACA GGAGGCUCAC AACAGGC      97
```

( 2 ) INFORMATION FOR SEQ ID NO:16:

( i ) SEQUENCE CHARACTERISTICS:
      ( A ) LENGTH: 96 base pairs
      ( B ) TYPE: nucleic acid
      ( C ) STRANDEDNESS: single
      ( D ) TOPOLOGY: linear ( i i ) MOLECULE TYPE: RNA ( x i ) SEQUENCE DESCRIPTION: SEQ ID NO:16:

GGGAGACAGA AUAAACGCUC AAAUCCCACU CGGUCGUGAC CUGACGUGAA 50

AACGGAUAGG AUCGCACGUC AAUUCGACAG GAGGCUCACA ACAGGC 96

( 2 ) INFORMATION FOR SEQ ID NO:17:

( i ) SEQUENCE CHARACTERISTICS:
      ( A ) LENGTH: 97 base pairs
      ( B ) TYPE: nucleic acid
      ( C ) STRANDEDNESS: single
      ( D ) TOPOLOGY: linear ( i i ) MOLECULE TYPE: RNA ( x i ) SEQUENCE DESCRIPTION: SEQ ID NO:17:

GGGAGACAAG AAUAAACGCU CAAGUGUCCC UUGUCACCUG GACUGGGCC 50

GUUUGAACUG ACAUUCUAUA CGAUUCGACA GGAGGCUCAC AACAGGC 97

( 2 ) INFORMATION FOR SEQ ID NO:18:

( i ) SEQUENCE CHARACTERISTICS:
      ( A ) LENGTH: 97 base pairs
      ( B ) TYPE: nucleic acid
      ( C ) STRANDEDNESS: single
      ( D ) TOPOLOGY: linear ( i i ) MOLECULE TYPE: RNA ( x i ) SEQUENCE DESCRIPTION: SEQ ID NO:18:

GGGAGACAAG AAUAAACGCU CAAGGCCAAC GUCCGAGUUG GUUUCCCAUA 50

GCUGAGCACA GGACGGCUUC UGCUUCGACA GGAGGCUCAC AACAGGC 97

( 2 ) INFORMATION FOR SEQ ID NO:19:

( i ) SEQUENCE CHARACTERISTICS:
      ( A ) LENGTH: 97 base pairs
      ( B ) TYPE: nucleic acid
      ( C ) STRANDEDNESS: single
      ( D ) TOPOLOGY: linear ( i i ) MOLECULE TYPE: RNA ( x i ) SEQUENCE DESCRIPTION: SEQ ID NO:19:

GGGAGACAAG AAUAAACGCU CAACCCGGAU GGUGAGCCCU GUCGGAGAUU 50

GGCACGAGGG UAAAGGGUAG GGAUUCGACA GGAGGCUCAC AACAGGC 97

( 2 ) INFORMATION FOR SEQ ID NO:20:

( i ) SEQUENCE CHARACTERISTICS:
      ( A ) LENGTH: 97 base pairs
      ( B ) TYPE: nucleic acid
      ( C ) STRANDEDNESS: single
      ( D ) TOPOLOGY: linear ( i i ) MOLECULE TYPE: RNA ( x i ) SEQUENCE DESCRIPTION: SEQ ID NO:20:

GGGAGACAAG AAUAAACGCU CAACUGUUGC UAAGUAGAAG UCAUAUUCUG 50

CGAUGGUUAA AGAUAACCCA GCCUUCGACA GGAGGCUCAC AACAGGC 97

( 2 ) INFORMATION FOR SEQ ID NO:21:

( i ) SEQUENCE CHARACTERISTICS:
        ( A ) LENGTH: 95 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:21:

GGGAGACAAG AAUAAACGCU CAAUCUCGUA UCAGCACACC GGUACAAAGA 50

GGAUGCAAAU NCGCCUGUGA CUUCGACAGG AGGCUCACAA CAGGC 95

( 2 ) INFORMATION FOR SEQ ID NO:22:

( i ) SEQUENCE CHARACTERISTICS:
        ( A ) LENGTH: 100 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:22:

GGGAGACAAG AAUAAACGCU CAACGUCUUC UACAGGGAAC CGUGGUGCAU 50

CUGUGAAGUU GUUGUAGAUU CCUAGAUUCG ACAGGAGGCU CACAACAGGC 100

( 2 ) INFORMATION FOR SEQ ID NO:23:

( i ) SEQUENCE CHARACTERISTICS:
        ( A ) LENGTH: 97 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:23:

GGGAGACAAG AAUAAACGCU CAAUGUCUUG GCGUCCACGU CGUAGUGUGU 50

GGGGGGAAAA GAGGAGGGUG CACUUCGACA GGAGGCUCAC AACAGGC 97

( 2 ) INFORMATION FOR SEQ ID NO:24:

( i ) SEQUENCE CHARACTERISTICS:
        ( A ) LENGTH: 97 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:24:

GGGAGACAAG AAUAAACGCU CAAUUGUUAG CCUGGUGAAG CAUGUACUGC 50

GAAGUGGAGG GAAUGUGGAA GGGUUCGACA GGAGGCUCAC AACAGGC 97

( 2 ) INFORMATION FOR SEQ ID NO:25:

( i ) SEQUENCE CHARACTERISTICS:
        ( A ) LENGTH: 97 base pairs
        ( B ) TYPE: nucleic acid
        ( C ) STRANDEDNESS: single (D) TOPOLOGY: linear (i i) MOLECULE TYPE: RNA (x i) SEQUENCE DESCRIPTION: SEQ ID NO:25:

```
GGGAGACAAG AAUAAACGCU CAAGCUCCCC UAGCCGACUU CCUGUUGGAC    50
GAGGGUGGUA CCGUGGGAGG AUGUUCGACA GGAGGCUCAC AACAGGC       97
```

(2) INFORMATION FOR SEQ ID NO:26:

(i) SEQUENCE CHARACTERISTICS:
  (A) LENGTH: 97 base pairs
  (B) TYPE: nucleic acid
  (C) STRANDEDNESS: single
  (D) TOPOLOGY: linear (i i) MOLECULE TYPE: RNA (x i) SEQUENCE DESCRIPTION: SEQ ID NO:26:

```
GGGAGACAAG AAUAAACGCU CAACGAGCCU UUAGUAAGAC UCAUGCCGAG    50
AAAUCGGUCG UGAUGCUGUC GAGUUCGACA GGAGGCUCAC AACAGGC       97
```

(2) INFORMATION FOR SEQ ID NO:27:

(i) SEQUENCE CHARACTERISTICS:
  (A) LENGTH: 97 base pairs
  (B) TYPE: nucleic acid
  (C) STRANDEDNESS: single
  (D) TOPOLOGY: linear (i i) MOLECULE TYPE: RNA (x i) SEQUENCE DESCRIPTION: SEQ ID NO:27:

```
GGGAGACAAG AAUAAACGCU CAAUUCGUGA GGGCGGUGUG GGAGGCAAGC    50
GGUACGAGCG UACUGUCUGG GCCUUCGACA GGAGGCUCAC AACAGGC       97
```

(2) INFORMATION FOR SEQ ID NO:28:

(i) SEQUENCE CHARACTERISTICS:
  (A) LENGTH: 98 base pairs
  (B) TYPE: nucleic acid
  (C) STRANDEDNESS: single
  (D) TOPOLOGY: linear (i i) MOLECULE TYPE: DNA (x i) SEQUENCE DESCRIPTION: SEQ ID NO:28:

```
GGGAAAAGCG AATCATACAC AAGANNNNN NNNNNNNNN NNNNNNNNN        50
NNNNNNNNN NNNNNNNNN NNNNGCTCCG CCAGAGACCA ACCGAGAA         98
```

(2) INFORMATION FOR SEQ ID NO:29:

(i) SEQUENCE CHARACTERISTICS:
  (A) LENGTH: 41 base pairs
  (B) TYPE: nucleic acid
  (C) STRANDEDNESS: single
  (D) TOPOLOGY: linear (i i) MOLECULE TYPE: DNA (x i) SEQUENCE DESCRIPTION: SEQ ID NO:29:

```
TAATACGACT CACTATAGGG AAAAGCGAAT CATACACAAG A              41
```

(2) INFORMATION FOR SEQ ID NO:30:

(i) SEQUENCE CHARACTERISTICS:

( A ) LENGTH: 24 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:30:

TTCTCGGTTG GTCTCTGGCG GAGC 24

( 2 ) INFORMATION FOR SEQ ID NO:31:

( i ) SEQUENCE CHARACTERISTICS:
( A ) LENGTH: 98 base pairs
( B ) TYPE: nucleic acid
( C ) STRANDEDNESS: single
( D ) TOPOLOGY: linear ( i i ) MOLECULE TYPE: RNA ( x i ) SEQUENCE DESCRIPTION: SEQ ID NO:31:

GGGAAAAGCG AAUCAUACAC AAGANNNNN NNNNNNNNN NNNNNNNNN 50

NNNNNNNNN NNNNNNNNN NNNNGCUCCG CCAGAGACCA ACCGAGAA 98

( 2 ) INFORMATION FOR SEQ ID NO:32:

( i ) SEQUENCE CHARACTERISTICS:
( A ) LENGTH: 50 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:32:

CGCGGATCCT AATACGACTC ACTATAGGGA AAAGCGAATC ATACACAAGA 50

( 2 ) INFORMATION FOR SEQ ID NO:33:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:33:

GGCGAATTCT TCTCGGTTGG TCTCTGGCGG AGC 33

( 2 ) INFORMATION FOR SEQ ID NO:34:

( i ) SEQUENCE CHARACTERISTICS:
( A ) LENGTH: 97 base pairs
( B ) TYPE: nucleic acid
( C ) STRANDEDNESS: single
( D ) TOPOLOGY: linear ( i i ) MOLECULE TYPE: RNA ( x i ) SEQUENCE DESCRIPTION: SEQ ID NO:34:

GGGAAAAGCG AAUCAUACAC AAGAUGUGAU GGGUGUGUUU UGGUUAGCUG 50

UGGAGGGCCA UGUGGGCUGG ACGGCUCCGC CAGAGACCAA CCGAGAA 97

( 2 ) INFORMATION FOR SEQ ID NO:35:

( i ) SEQUENCE CHARACTERISTICS:
( A ) LENGTH: 98 base pairs ( B ) TYPE: nucleic acid
( C ) STRANDEDNESS: single
( D ) TOPOLOGY: linear ( i i ) MOLECULE TYPE: RNA ( x i ) SEQUENCE DESCRIPTION: SEQ ID NO:35:

GGGAAAAGCG AAUCAUACAC AAGAGGUGUG UGUGCGCCGC GAGGUGUCUG 50

AGGAGAGAGG UGGCAGUGGA GGGUGCUCCG CCAGAGACCA ACCGAGAA 98

( 2 ) INFORMATION FOR SEQ ID NO:36:

( i ) SEQUENCE CHARACTERISTICS:
( A ) LENGTH: 98 base pairs
( B ) TYPE: nucleic acid
( C ) STRANDEDNESS: single
( D ) TOPOLOGY: linear ( i i ) MOLECULE TYPE: RNA ( x i ) SEQUENCE DESCRIPTION: SEQ ID NO:36:

GGGAAAAGCG AAUCAUACAC AAGAGGAGGG UGUGCGGACG GGAGCGUGUA 50

GUGAGGCUUU UCAGGCGUUG GACGGCUCCG CCAGAGACCA ACCGAGAA 98

( 2 ) INFORMATION FOR SEQ ID NO:37:

( i ) SEQUENCE CHARACTERISTICS:
( A ) LENGTH: 98 base pairs
( B ) TYPE: nucleic acid
( C ) STRANDEDNESS: single
( D ) TOPOLOGY: linear ( i i ) MOLECULE TYPE: RNA ( x i ) SEQUENCE DESCRIPTION: SEQ ID NO:37:

GGGAAAAGCG AAUCAUACAC AAGAUGUGAU GGGUGUGAUU UUGGUUAGCU 50

GUGGAGGGUU AUGUGGGUCG GACGGCUCCG CCAGAGACCA ACCGAGAA 98

( 2 ) INFORMATION FOR SEQ ID NO:38:

( i ) SEQUENCE CHARACTERISTICS:
( A ) LENGTH: 98 base pairs
( B ) TYPE: nucleic acid
( C ) STRANDEDNESS: single
( D ) TOPOLOGY: linear ( i i ) MOLECULE TYPE: RNA ( x i ) SEQUENCE DESCRIPTION: SEQ ID NO:38:

GGGAAAAGCG AAUCAUACAC AAGAUGUGGG CUUCCUGAGG GGUAGGAACU 50

CUGAAGUCAU GGUUCGUGGU AAGCGCUCCG CCAGAGACCA ACCGAGAA 98

( 2 ) INFORMATION FOR SEQ ID NO:39:

( i ) SEQUENCE CHARACTERISTICS:
( A ) LENGTH: 98 base pairs
( B ) TYPE: nucleic acid
( C ) STRANDEDNESS: single
( D ) TOPOLOGY: linear ( i i ) MOLECULE TYPE: RNA ( x i ) SEQUENCE DESCRIPTION: SEQ ID NO:39:

GGGAAAAGCG AAUCAUACAC AAGAGGAGGG AAUGUGGAAG GGUUUGUGGU 50

GUUUCGCAAA UGCCGCAUGG ACGUGCUCCG CCAGAGACCA ACCGAGAA 98

(2) INFORMATION FOR SEQ ID NO:40:

(i) SEQUENCE CHARACTERISTICS:
      (A) LENGTH: 98 base pairs
      (B) TYPE: nucleic acid
      (C) STRANDEDNESS: single
      (D) TOPOLOGY: linear (ii) MOLECULE TYPE: RNA (xi) SEQUENCE DESCRIPTION: SEQ ID NO:40:

```
GGGAAAAGCG AAUCAUACAC AAGAGGGGGG AGAGGCGUGG ACGAUGUUGU    50
GGUUAUGCUG UCGGUUUUGG CUUGGCUCCG CCAGAGACCA ACCGAGAA      98
```

(2) INFORMATION FOR SEQ ID NO:41:

(i) SEQUENCE CHARACTERISTICS:
      (A) LENGTH: 98 base pairs
      (B) TYPE: nucleic acid
      (C) STRANDEDNESS: single
      (D) TOPOLOGY: linear (ii) MOLECULE TYPE: RNA (xi) SEQUENCE DESCRIPTION: SEQ ID NO:41:

```
GGGAAAAGCG AAUCAUACAC AAGAGGGAUG GAUCGGUGAG ACGAGCAGUG    50
GAGUGGUGAG GUGUGGUGUC ACGUGCUCCG CCAGAGACCA ACCGAGAA      98
```

(2) INFORMATION FOR SEQ ID NO:42:

(i) SEQUENCE CHARACTERISTICS:
      (A) LENGTH: 98 base pairs
      (B) TYPE: nucleic acid
      (C) STRANDEDNESS: single
      (D) TOPOLOGY: linear (ii) MOLECULE TYPE: RNA (xi) SEQUENCE DESCRIPTION: SEQ ID NO:42:

```
GGGAAAAGCG AAUCAUACAC AAGACGUUCG GUGGUGGACA GGGUAAUGUG    50
GAGGGACCGG GUGAUUGUGU AUGUGCUCCG CCAGAGACCA ACCGAGAA      98
```

(2) INFORMATION FOR SEQ ID NO:43:

(i) SEQUENCE CHARACTERISTICS:
      (A) LENGTH: 98 base pairs
      (B) TYPE: nucleic acid
      (C) STRANDEDNESS: single
      (D) TOPOLOGY: linear (ii) MOLECULE TYPE: RNA (xi) SEQUENCE DESCRIPTION: SEQ ID NO:43:

```
GGGAAAAGCG AAUCAUACAC AAGAUGGAGG GUGGCGGGAG AAGUUUGAGG    50
UCGGGGUCGU AUGAUGUGCG CUAGGCUCCG CCAGAGACCA ACCGAGAA      98
```

(2) INFORMATION FOR SEQ ID NO:44:

(i) SEQUENCE CHARACTERISTICS:
      (A) LENGTH: 98 base pairs
      (B) TYPE: nucleic acid
      (C) STRANDEDNESS: single
      (D) TOPOLOGY: linear (ii) MOLECULE TYPE: RNA (xi) SEQUENCE DESCRIPTION: SEQ ID NO:44:

```
GGGAAAAGCG  AAUCAUACAC  AAGAUCACGA  CGGAGGGCGG  AUGAAGGGGG  50

GAAGGUCGUG  AGUCCAUGCC  GUGUGCUCCG  CCAGAGACCA  ACCGAGAA    98
```

( 2 ) INFORMATION FOR SEQ ID NO:45:

( i ) SEQUENCE CHARACTERISTICS:
        ( A ) LENGTH: 97 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:45:

```
GGGAAAAGCG  AAUCAUACAC  AAGAGGAUGG  GCGUGAAUGG  AGGGCAAUGU  50

GUGGGUUUGU  UGAGCCAGUU  GGUGCUCCGC  CAGAGACCAA  CCGAGAA     97
```

( 2 ) INFORMATION FOR SEQ ID NO:46:

( i ) SEQUENCE CHARACTERISTICS:
        ( A ) LENGTH: 98 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:46:

```
GGGAAAAGCG  AAUCAUACAC  AAGAACGGGU  CCCUAAGACG  UCGUUUCGAG  50

AUGUGUGUUU  CGGAAAGAGU  AGCGGCUCCG  CCAGAGACCA  ACCGAGAA    98
```

( 2 ) INFORMATION FOR SEQ ID NO:47:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:47:

```
AGGAGAGAGA  UGGGUGCGAG  AGCGU       25
```

HIGH AFFINITY HIV-1 GAG NUCLEIC ACID LIGANDS

RELATED APPLICATIONS

This application is a Continuation-in-Part of U.S. patent application Ser. No. 07/714,131, filed Jun. 10, 1991, entitled Methods for Identifying Nucleic Acid Ligands now issued as U.S. Pat. No. 5,475,096, U.S. patent application Ser. No. 07/931,473, filed Aug. 17, 1992, entitled Nucleic Acid Ligands, now issued as U.S. Pat. No. 5,270,163, U.S. patent application Ser. No. 07/964,624, filed Oct. 21, 1992, entitled Nucleic Acid Ligands now issued as U.S. Pat. No. 5,476,938, and U.S. patent application Ser. No. 08/117,991, filed Sep. 8, 1993, entitled High Affinity Nucleic Acid Ligands Containing Modified Nucleotides, now abandoned. U.S. patent application Ser. No. 07/714,131 is a Continuation-in-Part of U.S. patent application Ser. No. 07/536,428, filed Jun. 11, 1990, entitled Systematic Evolution of Ligands by EXponential Enrichment, now abandoned.

FIELD OF THE INVENTION

Described herein are methods for identifying and preparing high-affinity nucleic acid ligands to HIV-1 GAG. The method utilized herein for identifying such nucleic acid ligands is called SELEX, an acronym for Systematic Evolution of Ligands by EXponential enrichment. This invention includes high affinity nucleic acid ligands of HIV-1 GAG. Further disclosed are RNA ligands to HIV-1 GAG. The oligonucleotides of the present invention are useful as pharmaceuticals or diagnostic agents.

BACKGROUND OF THE INVENTION

The type-1 human immunodeficiency virus (HIV-1) is the etiological agent of acquired immunodeficiency syndrome (AIDS) (Levy (1993) Microbiol. Rev. 57: 183–289). There are estimated to be about 1 million people infected with HIV-1 in the United States and over 13 million worldwide. In some localities over 80% of the population is infected. The average time between HIV-1 infection and death is about ten years, making the course of treatment long and expensive. There is no cure for HIV-1 infection. Four mononucleoside drugs (AZT, ddI, ddC, and d4T) have been approved for use in the United States for the treatment of HIV-1 infection. Each of these drugs inhibits the HIV-1 reverse transcriptase protein. However, the usefulness of these drugs is limited by the rapid emergence of drug resistance mutants (Larder (1989) Science 246: 1155–1158). More effective treatments or a cure for HIV-1 infection would be highly desirable. As a result, other HIV-1 proteins, such as HIV-1 protease, are being explored as possible drug targets (Huff (1991) J. Med. Chem. 34: 2305–2314; Kempf (1995) Proc. Natl. Acad. Sci. USA 92: 2484–2488).

The HIV-1 gag (group specific antigen; also called assemblin) protein is a polyprotein composed of several HIV-1 proteins including matrix, capsid, p1, p2, p6, and nucleocapsid. Gag is myristylated on the N-terminus. Myristylation is required for localization of gag to the inner surface of the plasma membrane. Once gag accumulates to a high enough concentration at the membrane it begins to multimerize. Multimerization of gag results in the formation of an immature virion that is released from the cell. After release of the virion, gag is processed into individual proteins by the HIV-1 protease leading to the formation of what is referred to as the mature virion. From electron microscopy studies, gag appears to be a cylindrical -shaped protein that is 85 Å long and 34 Å wide (Nurmut et al. (1994) Virology 198: 288–296). There are estimated to be about 2000 gag proteins per virus.

The HIV-1 gag protein has multiple functions in the life cycle of HIV-1 that are reflective of the functions of its individual protein components. Gag contains the structural proteins of HIV-1 and most of the functions of gag revolve around packaging of the viral RNA and assembly of the virus (Gelderblom (1991) AIDS 5: 617–638).

The matrix protein component of gag is thought to mediate protein/protein interactions that direct the assembly and multimerization of the "core" of HIV-1. The NMR structure of matrix is known and resembles that of gamma interferon (Matthews (1994) Nature 370: 666–668). Matrix is required early after infection for entry of viral DNA into the nucleus (Buckrinsky et al. (1992) Proc. Natl. Acad. Sci. USA 89: 6580–6584). It has a classic lysine-rich nuclear localization signal, but tyrosine phosphorylation may be required for nuclear import (Gallay et al. (1995) Cell 80: 379–388).

The capsid protein ultimately forms the electron dense, cone-shaped core of HIV-1. Capsid binds stoichiometrically to cyclophilin A, a cellular protein, leading to its incorporation into mature HIV-1 particles (Luban et al. (1994) Cell 73: 1067–1078; Thali et al. (1994) Nature 372: 363–365; Franke et al. (1994) Nature 372: 359–362). Cyclophilin A is the target for the action of immunosuppressive drugs related to cyclosporin A. Cyclosporin A and non-immunosuppressive derivatives such as Sandoz NM811 prevent cyclophilin A incorporation into HIV-1 and severely reduce HIV infectivity (Steinkasserer et al. (1995) J. Virol. 69: 814–824). Mutants of capsid that do not bind cyclophilin A are also noninfectious.

The peptides p1 and p2 are cleaved from gag during its proteolytic processing and are thought to be involved in regulation of proteolysis, but they may also have other functions.

The nucleocapsid protein packages HIV-1 RNA into assembling viruses. Both nucleocapsid and gag bind to a specific region called Ψ that is about 200 bases long and is located at the 5' end of the HIV-1 RNA (Aldovini and Young (1990) J. Virol. 64: 1920–1926; Luban and Goff (1991) J. Virol. 65: 3203–3212; Hayashi et al. (1992) Virology 188: 590–599; Berkowitz et al. (1993) J. Virol 67: 7190–7200; Richardson et al. (1993) J. Virol. 67: 3997–4005; Sakuguchi et al. (1993) Proc. Natl. Acad. Sci. USA 90: 5219–5223). Two HIV-1 RNAs are packaged into each virus in a parallel orientation. Dimerization of the RNA is mediated by a "dimer linkage site" that is thought to be within or overlapping Ψ (Darlix et al. (1990) J. Mol. Biol. 216: 689–699; Marquet et al. (1991) Nucl. Acid Res. 19: 153–159; Awang and Sen (1993) Biochem. 32: 11453–11457; Skripkin et al. (1994) Proc. Natl. Acad. Sci. USA 91: 4945–4949). It has been suggested that HIV-1 RNA dimerization may involve guanine quartet structures (Sundquist and Heaphy (1993) Proc. Natl. Acad. Sci. USA 90: 3393–3397). The RNA sequences within the Ψ region that are required for gag binding appear to overlap with those required for packaging of viral RNA (Luban and Goff (1994) J. Virol. 68: 3784–3793), but it isn't clear yet if sequences required for gag binding and packaging are identical. Nucleocapsid binding to Ψ requires two zinc finger domains and a basic region (Doffmann et al. (1993) J. Virol. 67: 6159–6169; Dannull et al. (1994) EMBO J. 13: 1525–1533). The structure of nucleocapsid has been determined by nuclear magnetic resonance spectroscopy (Morellet et al. (1994) J. Mol. Biol. 235: 287–301).

The p6 protein binds the HIV-1 vpr protein leading to its stoichiometric incorporation into viruses (Paxton et al. (1993) J. Virol. 67: 7229–7237). Vpr is involved in the nuclear localization of viral DNA prior to chromosomal integration. Vpr and p6 both lack a classical nuclear localization signal so it has not been clear how they become localized in the nucleus. However, recently it has been reported that vpr may bind to the glucocorticoid receptor which can translocate to the nucleus (Refaeli et al. (1995) Proc. Natl. Acad. Sci. USA 92: 3621–3625). The p6 protein may also play a role in budding of viruses from cells since mutants that lack p6 are defective in budding (Gottlinger et at. (1991) Proc. Natl. Acad. Sci. USA 88: 3195–3199).

A method for the in vitro evolution of nucleic acid molecules with highly specific binding to target molecules has been developed. This method, Systematic Evolution of Ligands by EXponential enrichment, termed SELEX, is described in U.S. patent application Ser. No. 07/536,428, entitled "Systematic Evolution of Ligands by Exponential Enrichment," now abandoned, U.S. patent application Ser. No. 07/714,131, filed Jun. 10, 1991, entitled "Nucleic Acid Ligands," now issued as U.S. Pat. No. 5,475,096 U.S. patent application Ser. No. 07/931,473, filed Aug. 17, 1992, entitled "Methods for Identifying Nucleic Acid Ligands," now U.S. Pat. No. 5,270,163 (see also PCT application publication No. WO 91/19813), each of which is herein specifically incorporated by reference. Each of these applications, collectively referred to herein as the SELEX Patent Applications, describes a fundamentally novel method for making a nucleic acid ligand to any desired target molecule.

The SELEX method involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific, high affinity nucleic acid ligands to the target molecule.

The basic SELEX method has been modified to achieve a number of specific objectives. For example, U.S. patent application Ser. No. 07/960,093, filed Oct. 14, 1992, entitled "Method for Selecting Nucleic Acids on the Basis of Structure," describes the use of SELEX in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands" describes a SELEX based method for selecting nucleic acid ligands containing photoreactive groups capable of binding and/or photocrosslinking to and/or photoinactivating a target molecule. U.S. patent application Ser. No. 08/134,028, filed Oct. 7, 1993, entitled "High-Affinity Nucleic Acid Ligands That Discriminate Between Theophylline and Caffeine," describes a method for identifying highly specific nucleic acid ligands able to discriminate between closely related molecules, termed Counter-SELEX. U.S. patent application Ser. No. 08/143,564, filed Oct. 25, 1993, entitled "Systematic Evolution of Ligands by EXponential Enrichment: Solution SELEX," now issued as U.S. Pat. No. 5,567,588 describes a SELEX-based method which achieves highly efficient partitioning between oligonucleotides having high and low affinity for a target molecule. U.S. patent application Ser. No. 07/964,624, filed Oct. 21, 1992, entitled "Nucleic Acid Ligands to HIV-RT and HIV-1 Rev," now issued as U.S. Pat. No. 5,496,938 describes methods for obtaining improved nucleic acid ligands after SELEX has been performed. U.S. patent application Ser. No. 08/400,440, filed Mar. 8, 1995, entitled "Systematic Evolution of Ligands by EXponential Enrichment: Chemi-SELEX," describes methods for covalently linking a ligand to its target.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified nucleic acid ligands containing modified nucleotides are described in U.S. patent application Ser. No. 08/117,991, filed Sep. 8, 1993, entitled "High Affinity Nucleic Acid Ligands Containing Modified Nucleotides," that describes oligonucleotides containing nucleotide derivatives chemically modified at the 5- and 2'-positions of pyrimidines. U.S. patent application Ser. No. 08/134,028, supra, describes highly specific nucleic acid ligands containing one or more nucleotides modified with 2'-amino (2'-$NH_2$), 2'-fluoro (2'-F), and/or 2'-O-methyl (2'-OMe). U.S. patent application Ser. No. 08/264,029, filed Jun. 22, 1994, entitled "Novel Method of Preparation of known and nisvel nucleosides by 2' Modified Pyrimidine Intramolecular Nucleophilic Displacement," describes oligonucleotides containing various 2'-modified pyrimidines.

The SELEX method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX" now issued as U.S. Pat. No. 5,637,459 and U.S. patent application Ser. No. 08/234,997, filed Apr. 28, 1994, entitled "Systematic Evolution of Ligands by Exponential Enrichment: Blended SELEX," respectively. These applications allow the combination of the broad array of shapes and other properties, and the efficient amplification and replication properties, of oligonucleotides with the desirable properties of other molecules. Each of the above described patent applications which describe modifications of the basic SELEX procedure are specifically incorporated by reference herein in their entirety.

SELEX ligands that bind to HIV-1 proteins provide another method of "intracellular immunization" (Baltimore (1988) Nature 335: 395–396) against HIV-1 that differs from other nucleic acid-based technologies such as antisense (Zamecnik et al. (1986) Proc. Natl. Acad. Sci. USA 83: 4143–4146; Chatterjee et at. (1992) Science 258: 1485–1488; Lisziewicz et al. (1992) Proc. Natl. Acad. Sci. USA 89: 11209–11213), decoys (Sullenger et al. (1990) Cell 63: 601–608), and ribozymes (Sarver et al. (1990) Science 247: 1222–1225; Rossi et al. (1992) AIDS Res. Human Retroviruses 8: 183–189), which have also been shown that they have potential for being effective in preventing HIV-1 replication. In previous work we have evolved RNA molecules that bind to the HIV-1 rev, tat, reverse transcriptase, and integrase. Here we report the use of the SELEX method to derive RNA molecules that bind to the HIV-1 gag polyprotein.

Gag is an attractive target for the development of SELEX ligands for several reasons. First gag is an RNA binding protein, which facilitates the in vitro evolution process. Second gag is found in the cytoplasm of a cell unlike its protein components (e.g., nucleocapsid) that are only found after viral release from the cell. This feature is an attractive one with regard to achieving intracellular immunization.

BRIEF SUMMARY OF THE INVENTION

The present invention includes methods of identifying and producing nucleic acid ligands to Human Immunodeficiency Virus 1 gag polyprotein (HIV-1 GAG) and homologous polyproteins and the nucleic acid ligands so identified and produced. For the purpose of this application, HIV-1 GAG refers to the polyprotein or any of its component parts (i.e., matrix, capsid, p1, p2, p6, and nucleocapsid). In particular, RNA sequences are provided that are capable of binding specifically to HIV-1 GAG. Specifically included in the invention are the RNA ligand sequences shown in Tables 2 and 4 (SEQ ID NOS: 8–27, 34–46).

Further included in this invention is a method of identifying nucleic acid ligands and nucleic acid ligand sequences to HIV-1 GAG comprising the steps of (a) preparing a candidate mixture of nucleic acids, (b) contacting the candidate mixture of nucleic acids with HIV-1 GAG, (c) partitioning between members of said candidate mixture on the basis of affinity to HIV-1 GAG, and (d) amplifying the selected molecules to yield a mixture of nucleic acids enriched for nucleic acid sequences with a relatively higher affinity for binding to HIV-1 GAG.

More specifically, the present invention includes the RNA ligands to HIV-1 GAG identified according to the above-described method, including those ligands shown in Tables 2 and 4 (SEQ ID NOS: 8–27, 34–46). Also included are RNA ligands to HIV-1 GAG that are substantially homologous to any of the given ligands and that have substantially the same ability to bind HIV-1 GAG and inhibit the function of HIV-1 GAG. Further included in this invention are nucleic acid ligands to HIV-1 GAG that have substantially the same structural form as the ligands presented herein and that have substantially the same ability to bind HIV-1 GAG and inhibit the function of HIV-1 GAG.

The present invention also includes modified nucleotide sequences based on the RNA ligands identified herein and mixtures of the same.

DETAILED DESCRIPTION OF THE INVENTION

This application describes high-affinity nucleic acid ligands to HIV-1 GAG identified through the method known as SELEX. SELEX is described in U.S. patent application Ser. No. 07/536,428, entitled Systematic Evolution of Ligands by EXponential Enrichment, now abandoned, U.S. patent application Ser. No. 07/714,131, filed Jun. 10, 1991, entitled Nucleic Acid Ligands, now issued as U.S. Pat. No. 5,475,096 U.S. patent application Ser. No. 07/931,473, filed Aug. 17, 1992, entitled Methods of Identifying Nucleic Acid Ligands, now U.S. Pat. No. 5,270,163, (see also PCT application publication No. WO 91/19813). These applications, each specifically incorporated herein by reference, are collectively called the SELEX Patent Applications.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer weakly binding sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for partitioning nucleic acids within a candidate mixture; and methods for amplifying partitioned nucleic acids to generate enriched candidate mixture. The SELEX Patent Applications also describe ligands obtained to a number of target species, including both protein targets where the protein is and is not a nucleic acid binding protein.

The nucleic acid ligands described herein can be complexed with a lipophilic compound (e.g., cholesterol) or attached to or encapsulated in a complex comprised of lipophilic components (e.g., a liposome). The complexed nucleic acid ligands can enhance the cellular uptake of the nucleic acid ligands by a cell for delivery of the nucleic acid ligands to their intracellular target. U.S. patent application Ser. No. 08/434,465, filed May 4, 1995, entitled "Nucleic Acid Ligand Complexes," which is incorporated in its entirety herein, describes a method for preparing a therapeutic or diagnostic complex comprised of a nucleic acid ligand and a lipophilic compound or a non-immunogenic, high molecular weight compound.

The methods described herein and the nucleic acid ligands identified by such methods are useful for both therapeutic and diagnostic purposes. Therapeutic uses include the treatment or prevention of diseases or medical conditions in human patients. Diagnostic utilization may include both in vivo or in vitro diagnostic applications. The SELEX method generally, and the specific adaptations of the SELEX method taught and claimed herein specifically, are particularly suited for diagnostic applications. SELEX identifies nucleic acid ligands that are able to bind targets with high affinity and with surprising specificity. These characteristics are, of course, the desired properties one skilled in the art would seek in a diagnostic ligand.

The nucleic acid ligands of the present invention may be routinely adapted for diagnostic purposes according to any number of techniques employed by those skilled in the art. Diagnostic agents need only be able to allow the user to identify the presence of a given target at a particular locale or concentration. Simply the ability to form binding pairs with the target may be sufficient to trigger a positive signal for diagnostic purposes. Those skilled in the art would also be able to adapt any nucleic acid ligand by procedures known in the art to incorporate a labeling tag in order to track the presence of such ligand. Such a tag could be used in a number of diagnostic procedures. The nucleic acid ligands to HIV-1 GAG described herein may specifically be used for identification of the HIV-1 GAG polyprotein.

SELEX provides high affinity ligands of a target molecule. This represents a singular achievement that is unprecedented in the field of nucleic acids research. The present invention applies the SELEX procedure to the specific target of HIV-1 GAG. In the Example section below, the experimental parameters used to isolate and identify the nucleic acid ligands to HIV-1 GAG are described.

In order to produce nucleic acids desirable for use as a pharmaceutical, it is preferred that the nucleic acid ligand (1) binds to the target in a manner capable of achieving the desired effect on the target; (2) be as small as possible to obtain the desired effect; (3) be as stable as possible; and (4) be a specific ligand to the chosen target. In most situations, it is preferred that the nucleic acid ligand have the highest possible affinity to the target.

In co-pending and commonly assigned U.S. patent application Ser. No. 07/964,624, filed Oct. 21, 1992, now issued as U.S. Pat. No. 5,496,938, methods are described for obtaining improved nucleic acid ligands after SELEX has been performed. The '938 Patent, entitled Methods of Producing Nucleic Acid Ligands to HIV-RT and HIV-1, is specifically incorporated herein by reference.

In the present invention, two SELEX experiments were performed in order to identify RNA with specific high affinity for HIV-1 GAG from degenerate libraries containing 50 random positions (50N) (Tables 1 and 3). This invention includes the specific RNA ligands to HIV-1 GAG shown in Tables 2 and 4 (SEQ ID NOS: 8–27, 34–46), identified by the methods described in Examples 1 and 2. This invention further includes RNA ligands to HIV-1 GAG which inhibit the function of HIV-1 GAG. The scope of the ligands covered by this invention extends to all nucleic acid ligands of HIV-1 GAG, modified and unmodified, identified according to the SELEX procedure. More specifically, this invention includes nucleic acid sequences that are substantially homologous to the ligands shown in Tables 2 and 4 (SEQ ID NOS.: 8–27, 34–46). By substantially homologous it is meant a degree of primary sequence homology in excess of 70%, most preferably in excess of 80%. A review of the sequence homologies of the ligands of HIV-1 GAG shown in Tables 2 and 4 (SEQ ID NOS.: 8–27, 34–46) shows that sequences with little or no primary homology may have substantially the same ability to bind HIV-1 GAG. For these reasons, this invention also includes nucleic acid ligands that have substantially the same structure and ability to bind HIV-1 GAG as the nucleic acid ligands shown in Tables 2 and 4 (SEQ ID NOS.: 8–27, 34–46). Substantially the same ability to bind HIV-1 GAG means that the affinity is within one or two orders of magnitude of the affinity of the ligands described herein. It is well within the skill of those of ordinary skill in the art to determine whether a given sequence—substantially homologous to those specifically described herein—has substantially the same ability to bind HIV-1 GAG.

Inhibition of HIV-1 GAG function by the SELEX-derived ligands includes inhibition of the function of the GAG polyprotein or any of component parts. For example, inhibition of matrix or capsid interactions could inhibit viral assembly. Inhibition of vpr incorporation could lead to viruses that would be unable to integrate and therefore unable to replicate in cells. Inhibition of cyclophilin incorporation would also be expected to lead to the production of noninfectious virus for reasons mentioned above. Inhibition of nucleocapsid function could inhibit viral RNA packaging which would lead to the formation of noninfectious virus.

This invention also includes the ligands as described above, wherein certain chemical modifications are made in order to increase the in vivo stability of the ligand or to enhance or mediate the delivery of the ligand. Examples of such modifications include chemical substitutions at the sugar and/or phosphate and/or base positions of a given nucleic acid sequence. See, e.g., U.S. patent application Ser. No. 08/117,991, filed Sep. 8, 1993, entitled High Affinity Nucleic Acid Ligands Containing Modified Nucleotides which is specifically incorporated herein by reference. Other modifications are known to one of ordinary skill in the art. Such modifications may be made post-SELEX (modification of previously identified unmodified ligands) or by incorporation into the SELEX process.

As described above, because of their ability to selectively bind HIV-1 GAG, the nucleic acid ligands to HIV-1 GAG described herein are useful as pharmaceuticals. This invention, therefore, also includes a method for treating HIV-1 by administration of a nucleic acid ligand capable of binding to HIV-1 GAG.

Therapeutic compositions of the nucleic acid ligands may be administered parenterally by injection, although other effective administration forms, such as intraarticular injection, inhalant mists, orally active formulations, transdermal iontophoresis or suppositories, are also envisioned. One preferred carrier is physiological saline solution, but it is contemplated that other pharmaceutically acceptable carriers may also be used. In one preferred embodiment, it is envisioned that the carrier and the ligand constitute a physiologically-compatible, slow release formulation. The primary solvent in such a carrier may be either aqueous or non-aqueous in nature. In addition, the carrier may contain other pharmacologically-acceptable excipients for modifying or maintaining the pH, osmolarity, viscosity, clarity, color, sterility, stability, rate of dissolution, or odor of the formulation. Similarly, the carrier may contain still other pharmacologically-acceptable excipients for modifying or maintaining the stability, rate of dissolution, release, or absorption of the ligand. Such excipients are those substances usually and customarily employed to formulate dosages for parental administration in either unit dose or multi-dose form.

Once the therapeutic composition has been formulated, it may be stored in sterile vials as a solution, suspension, gel, emulsion, solid, or dehydrated or lyophilized powder. Such formulations may be stored either in a ready to use form or requiring reconstitution immediately prior to administration. The manner of administering formulations containing nucleic acid ligands for systemic delivery may be via subcutaneous, intramuscular, intravenous, intranasal or vaginal or rectal suppository.

The following Examples are provided to explain and illustrate the present invention and are not intended to be limiting of the invention. Example 1 describes the various materials and experimental procedures used in Example 2. Example 2 describes the RNA ligands to HIV-1 GAG and the affinities the ligands have for HIV-1 GAG. Example 3 describes modified 2'-NH$_2$ pyrimidine RNA ligands to HIV-1 gag.

EXAMPLE 1

EXPERIMENTAL PROCEDURES

Materials.

The HIV-1 gag protein was a generous gift from Drs. Tristram Parslow and Jared Clever (Department of Pathology and the Department of Microbiology and Immunology, University of California, San Francisco, Calif. 94143-0506) The HIV-1 gag protein from HIV-1 strain LAI was expressed in *E. coli* TOPP3 cells as a fusion to glutathione S-transferase and purified as described (Clever et al. (1995) J. Virol. 69: 2101–2109). In the Examples, the fusion protein is referred to as gag. All other reagents, chemicals and plasmids were from commercial sources.

SELEX ligand generation.

SELEX ligands that bind to the HIV-1 gag polyprotein were derived in two SELEX experiments ("A" and "B") essentially as described in U.S. Pat. No. 5,270,163 (see also Tuerk and Gold (1990) Science 249: 505–510; Tuerk et al. (1992) Proc. Natl. Acad. Sci. USA 89: 6988–6992; Tuerk and MacDougal-Waugh (1993) Gene 137: 33–39; Tuerk et al. (1994) in *The Polymerase Chain Reaction*, eds. Ferre et al. (Birkhauser, Springer-Verlag, New York; Jenson et al. (1994) J. Mol. Biol. 235: 237–247) with the following modifications. SEQ ID NO: 1 was used as the starting template and SEQ ID NOS: 2 and 3 were used for the PCR primers for SELEX "A" and SEQ ID NO: 28 was used as the starting template and SEQ ID NOS: 29 and 30 was used as the PCR primers for SELEX "B." SELEX experiment "A" used a starting RNA pool of 8.4×10$^{14}$ molecules with 50 random bases (Table 1; SEQ ID NO: 4), a binding buffer that consisted of 50 mM Tris, pH 7.5, 200 mM KOAc, 5 mM MgCl$_2$, and avian myeloblastosis virus (Life Sciences, Inc., St. Petersburg, Fla.) as the reverse transcriptase. SELEX experiment "B" used a starting RNA pool of 7×10$^{14}$ molecules with 50 random bases (Table 3; SEQ ID NO: 31), a binding buffer that consisted of 50 mM Tris, pH 7.5, 140 mM KCl, 5 mM NaCl, 5 mM MgCl$_2$, and murine leukemia virus reverse transcriptase (Superscript, Gibco, Inc., Gaithersburg, Md.) as the reverse transcriptase. SELEX experiment "B" also utilized increasing concentrations of heparin (molecular weight 5,000, Calbiochem, Inc., San Diego, Calif.) to compete with nonspecifically binding RNAs in the pool for binding to gag. Both the "A" and the "B" SELEX used Taq polymerase (Perkin-Elmer Cetus, Inc., Norwalk, Conn.) to amplify cDNA products. Binding of RNA pools was for 5 minutes in SELEX "A" and for 10–15 minutes in SELEX "B." T7 RNA polymerase and 2'-hydroxyl nucleosides were used to transcribe the amplified cDNAs. Nitrocellulose partitioning was used for both SELEX experiments except for round 5 in SELEX "B." Column SELEX was used for round 5 in SELEX "B" as described infra.

Binding affinities of ribonucleic acid ligands for target HIV-1 proteins.

The binding affinities of ribonucleic acid ligands for the gag protein were measured by filtration as described (Tuerk and Gold (1990) Science 249: 505–510). Briefly, radiolabeled RNA was transcribed from a PCR-generated template using T7 RNA polymerase and α-$^{32}$P-ATP. The RNA (~200 fmol; ~10,000 cpm) was mixed with a 10,000 fold molar excess of yeast tRNA and then bound to gag at concentrations ranging from 10$^{-12}$ to 10$^{-6}$M at 37° C. for 5 minutes in a 30–60 µl reaction. The buffer used for binding is as described above. The reactions were vacuum-filtered through nitrocellulose filters (HAWP, Millipore, Inc.). A control with no gag added was also included for each RNA to correct for the amount of the RNA that binds to the nitrocellulose filter instead of gag. The amount of labeled RNA specifically retained on the filter by gag was determined, and the apparent K$_d$ of the protein for the RNA was obtained by plotting the amount of RNA specifically bound to gag vs. the concentration of the protein using Kaleidograph computer software (Synergy, Inc., Reading, Pa.).

The 456 base long Ψ RNA that was used as a positive control in RNA binding experiments was obtained by transcription of the plasmid pBsPVR789 (Luban and Goff (1991) J. Virol. 65: 3203–3212) after linearization with Xho I.

Subcloning of ligands.

The ligand pool from the appropriate round was amplified using PCR primers (Table 1; SEQ ID NOS: 5 and 6 for SELEX "A," and Table 3, SEQ ID NOS: 32 and 33 for SELEX "B") that have restriction enzyme recognition sites on the 5' and 3' ends. The PCR products were digested with the appropriate restriction enzyme (HindIII and BamHI for SELEX "A" and BamHI and EcoRI for SELEX "B") and then subcloned into pUC9 (BRL, Inc., Gaithersburg, Md.) that was also digested with the appropriate restriction enzymes. The ligation was transformed into *E. coli* strain DH5α.

Sequence analysis of clones.

Plasmids were prepared from the transformants using either the boiling method or the alkaline lysis method using art known techniques (see *Molecular Cloning: A Laboratory Manual* (Eds. Sambrook et al.) 1989). The plasmids were denatured with 0.5M NaOH, desalted on a 0.5 ml G-50 Sephadex spin column, and then used for sequencing. Sequences were determined using the Sequenase version 2.0 enzyme (U.S. Biochemical, Inc., Cleveland, Ohio) according to manufacturer's instructions. A DNA primer labeled with phosphorous-32 at the 5'-end and corresponding to the T7 promoter (Table 1; SEQ ID NO: 7) was used as the sequencing primer.

EXAMPLE 2

RNA LIGANDS TO HIV-1 GAG

In vitro evolution of RNAs that bind to gag.

A GST-gag fusion protein was used in both SELEX experiments. GST alone has a low affinity (K$_d$>10 µM) for random RNA, whereas GST-gag has a higher affinity (K$_d$= 0.1–1 µM) for random RNA. Therefore, as a result of the properties of the SELEX method, the evolved ligands bind to gag and not GST.

SELEX "A" was carried out for a total of 11 rounds. The sequence of the RNA pool was determined at rounds 5, 6, and 7 and found to be nonrandom. The $K_d$ of the round 10 pool was determined and found to be 1.5 nM. In the same experiment, the $K_d$ of Ψ, the HIV-1 gag-binding RNA element, was 1.1 nM. On the basis of the $K_d$ and the nonrandomness of the sequences, the ligand pools from rounds 8 and 10 were cloned into pUC9 for sequence analysis of individual ligands.

Sequences were obtained from 34 clones, 19 from round 8 and 15 from round 10. Twelve of the sequences were identical and are represented by ligand SW8.4 (SEQ ID NO: 10). One ligand, represented by ligand SW10.22 (SEQ ID NO: 22), was almost identical to the ligand SW8.4 family. Two other sequences were identical to ligand SW8.6 (SEQ ID NO: 11). Another ligand, SW8.27 (SEQ ID NO: 15) differs from SW8.6 by two bases. Ligands SW8.24 (SEQ ID NO: 13) and SW10.39 (SEQ ID NO: 26) differ by one base. In summary, from 34 clones, 23 (SEQ ID NOS: 8–27) unique sequences were obtained.

The 23 unique ligands were screened for binding to the HIV-1 gag protein at 0.1 nM and 10.0 nM gag, concentrations that bracket the average Kd of the round 10 pool. Round 0 and Ψ RNA were added as negative and positive controls, respectively, for binding to gag, and all of the ligands were also filtered in the absence of gag to detect nitrocellulose binding sequences. The binding was done in the presence of a 10,000 fold molar excess of yeast tRNA. Three ligands were found to be nitrocellulose binders. The data for the 20 ligands that bound to gag are summarized in Table 5. Several ligands bound well to gag, especially the most frequent ligand SW 8.4 (and the related ligand SW 10.22), SW 8.1, SW 8.27, and SW 10.28.

It has been reported previously that ligands which bind to nitrocellulose filters are rich in guanine. The gag ligands from SELEX "A" that bound to nitrocellulose had 18 or more guanines in the randomized region, whereas the gag ligands that bound to gag had 14 or less guanines in the randomized region. The sequences of 20 clones from rounds 8 and 10 of SELEX "A" that bound to the gag protein are shown in Table 2.

SELEX "B" was carried out for a total of 9 rounds. After 4 rounds of SELEX, the amount of RNA that was binding to nitrocellulose filters had risen. Therefore, we employed an alternate partitioning strategy for round 5. Round 5 was performed using "column SELEX." 0 or 10 nmoles gag was bound to 50 μl glutathione Sepharose 4B (Pharmacia) on ice for 15 minutes. 150 nmoles of round 5 RNA pool was added and incubated at 37° C. for 15 minutes. The beads were pelleted in a microfuge at 1000 rpm for 2 minutes. The aqueous supernatant was saved. The pelleted beads were washed in 1 ml of ice cold binding buffer and then the beads were immediately repelleted. The beads were washed in such a manner for a total of 6 times. All of the washes and the beads were Cherenkov-counted. At this point, the beads incubated with gag bound 180 fmoles RNA, while the beads with no gag prebound had bound 3.3 fmoles RNA. The beads were then washed with 2–250 μl aliquots of binding buffer containing 5 mM reduced glutathione to elute gag/RNA complexes. The eluted gag/RNA complexes were phenol extracted, ethanol precipitated and the recovered RNA was reverse transcribed, amplified by PCR, and transcribed (as described in Tuerk and Gold (1990) Science 249: 505–510) in preparation for the round 6 selection. The enrichment of ligands in this round was calculated to be as much as 830 fold, substantially more than that for other rounds in which a standard nitrocellulose partitioning was used (average of about 100 fold enrichment).

The sequence of the RNA pool was determined at rounds 0, 2, 4, 6, and 8. The sequences of rounds 0, 2, and 4 were random. The sequences of the RNA pool from rounds 6 and 8 were nonrandom. The degree of enrichment that may have been achieved in round 5 may explain the sudden shift in the sequence of the RNA pools from random in round 4 to nonrandom in round 6.

The $K_d$ of the round 0, 4, and 8 pools was determined and found to be ~1 μM, 8.5 nM, and 1.1 nM, respectively. In the same experiment, the $K_d$ of Ψ, the HIV-1 gag binding RNA element, was 5.2 nM.

The ability of Ψ, round 4, and round 8 RNA pools from SELEX "B" to compete with Ψ for binding to gag was examined. The concentration of $^{32}$P-labeled Ψ, round 4, and round 8 RNA pools was approximately 150 pM, the concentration of gag was fixed at approximately 1 nM, and the concentration of unlabeled Ψ was varied. The amount of unlabeled Ψ required to compete off 50% of the $^{32}$P-labeled Ψ, round 4, or round 8 RNA pools was a 20, 74 or 630 fold excess, respectively. Therefore, SELEX ligands can compete for binding to gag more effectively than Ψ. Since SELEX-derived gag ligands have a lower $K_d$ for gag than Ψ and since they compete more effectively for binding than does Ψ, in a gene therapy setting, SELEX-derived gag ligands may not need to be expressed to a level comparable to the HIV-1 RNA in order to effectively compete for binding to gag.

On the basis of the $K_d$ and the nonrandomness of the sequence pools after round 6, the ligand pool from round 8 was subcloned into pUC9 for sequence analysis of individual ligands.

The sequences of 16 clones from round 8 of SELEX "B" were determined (Table 4). Three of the sequences were identical to ligand ML8.7 (SEQ ID NO: 34) and two represented by ligand ML8.14 (SEQ ID NO: 37) were similar to ligand ML8.7. Therefore, a total of 13 unique sequences (SEQ ID NOS: 34–46) were obtained. These sequences have not been tested for binding to the gag protein; however, since the ML8.7 ligand was frequent in the population it is most likely a ligand that binds to the gag protein (as was the case for ligand SW8.4).

Both SELEX "A" and "B" had a ligand that was more frequent in occurence than the others. In SELEX "A" the most frequent ligand was represented by SW8.4 (SEQ ID NO: 10). This clone or closely related ligands were present in 13 of 34 sequences obtained. In SELEX "B", the most frequent ligand was ML8.7 (SEQ ID NO: 34). This clone or closely related ligands were represented in 5 of 16 sequences obtained. Thus in each SELEX experiment about 30–40% of the clones were a single dominant ligand. The most frequent clones from each of the two SELEX experiments were not highly similar to each other (17/50 bases when optimally aligned). This was expected since different templates and conditions were used in the two SELEXs.

By employing the method of SELEX, it is possible to evolve ligands that are similar or almost identical to natural RNA elements that bind to HIV-1 proteins. Therefore, we examined the gag ligands for similarity to the Ψ element and to the entire HIV-1 LAI sequence. One ligand, ML8.11 (SEQ ID NO: 35), has a stretch of 19 bases out of 24 that are identical (shown in bold below) to a region of HIV-1 Ψ, which is located in the region surrounding the HIV-1 gag translation initiation site (underlined below).

part of ligand ML8.11(SEQ ID NO: 35): . . . AGGAGAGAGGUGGCAGUG-GAGGGU . . .

part of HIV-1 Ψ region (SEQ ID NO: 47): . . . AGGAGAGAGAUGGGUGCGAGAGCGU . . .

EXAMPLE 3

MODIFIED 2'-NH2 PYRIMIDINE RNA LIGANDS TO HIV-1 GAG.

In order to generate ligands with improved stability in vivo, an experiment is carried out with randomized RNA containing $NH_2$ functionalities at the 2'-position of each pyrimidine. A library of $7-9 \times 10^{14}$ molecules is generated that contains 50 nucleotides of contiguous random sequence flanked by defined sequences. Defined nucleotide sequences in the flanking regions of the template can serve as primer annealing sites for PCR and with one of the primers providing the T7 promoter sequence (a restriction site can be added for cloning). The random and fixed nucleotides of the initial candidate mixture are comprised of 2'-$NH_2$ pyrimidine bases. The round of selection and amplification are carried out as described supra in Examples 1-2 using art-known techniques.

TABLE 1

Starting template sequence for SELEX "A".
5'-GGGAGACAAGAATAAACGCTCAA-50N-TTCGACAGGAGGCTCACAACAGGC-3' (SEQ ID NO: 1)
5' PCR primer for SELEX "A":
5'-TAATACGACTCACTATAGGGAGACAAGAATAAACGCTCAA-3' (SEQ ID NO:2)
3' PCR primer for SELEX "A":
5'-GCCTGTTGTGAGCCTCCTGTCGAA-3' (SEQ ID NO:3)
Starting RNA sequence pool for SELEX "A":
5'-GGGAGACAAGAAUAAACGCUCAA-50N-UUCGACAGGAGGCUCACAACAGGC-3' (SEQ ID NO:4)
5' primer for cloning evolved ligands from SELEX "A":
5'-GCCGGATCCGCCTGTTGTGAGCCTCCTGTCGAA-3' (SEQ ID NO: 5)
3' primer for cloning evolved ligands from SELEX "A":
5'-CCGAAGCTTAATACGACTCACTATAGGGAGACAAGAATAAACGCTCAA-3' (SEQ ID NO:6)
primer for sequencing cloned ligands from SELEX "A"and "B":
5' TAATACGACTCACTATA 3' (SEQ ID NO:7)

TABLE 2

Evolved gag ligands from SELEX experiment "A"
5'-GGGAGACAAGAAUAAACGCUCAA-50N-UUCGACAGGAGGCUCACAACAGGC-3' (SEQ ID NO: 4)

| Sequence ID no: | Ligand Name | Sequence of randomized region |
|---|---|---|
| 8 | SW8.1 | UUGUGAUCUACCGUUACCUGACGGACGUGUUUUUACACCAACGAACCUGG |
| 9 | SW8.2 | UGAACCUCUGAGUUCUUCAUAGAACUGAUAUCUUCAAGAAGGGGUAGAUG |
| 10 | SW8.4 | CGUCUUCUACAGGGAACCGUGGUGCAUCUGUGAAGUUGUAGAUUCCUAGU |
| 11 | SW8.6 | GGGUUGAUUACCAAAUCGUAACCUGUACCCUGCCUACACUAGGACAACGG |
| 12 | SW8.20 | CUAACCGAAGCUCUGAGAAAUAGUUUAUCCAGUGAAUGAAUCCUGAUGGG |
| 13 | SW8.24 | CGAGCUUUUAGUAAGACUCAUGCCGAGAAAUCGGUCGUGAUGCUGUCGAG |
| 14 | SW8.25 | GCCCGGGAAUUGCAUGUUGUGCGUGCCGGGAGUCCAAGUCAGCAUCCUCA |
| 15 | SW8.27 | GGGUUGAUUACCAAAUCGUAACCUGUACCCUGCCUACCCUAGGACAACGA |
| 16 | SW8.30* | AUCCCACUCGGUCGUGACCUGACGUGAAAACGGAUAGGAUCGCACGUCAA |
| 17 | SW8.31 | GUGUCCCUUGUCACCUGGGACUGGGCCGUUUGAACUGACAUUCUAUACGA |
| 18 | SW8.37 | GGCCAACGUCCGAGUUGGUUUCCCAUAGCUGAGCACAGGACGGCUUCUGC |
| 19 | SW8.40 | CCCGGAUGGUGAGCCCUGUCGGAGAUUGGCACGAGGGUAAAGGGUAGGGA |
| 20 | SW10.7 | CUGUUGCUAAGUAGAAGUCAUAUUCUGCGAUGGUUAAAGAUAACCCAGCC |
| 21 | SW10.12 | UCUCGUAUCAGCACACCGGUACAAAGAGGAUGCAAAUNCGCCUGUGAC |
| 22 | SW10.22 | CGUCUUCUACAGGGAACCGUGGUGCAUCUGUGAAGUUGUUGUAGAUUCCUAGA |
| 23 | SW10.25 | UGUCUUGGCGUCCACGUCGUAGUGUGUGGGGGGAAAAGAGGAGGGUGCAC |
| 24 | SW10.28 | UUGUUAGCCUGGUGAAGCAUGUACUGCGAAGAUGGAGGGAAUGUGGAAGGG |
| 25 | SW10.34 | GCUCCCCUAGCCGACUUCCUGUUGGACGAGGGUGGUACCGUGGGAGGAUG |
| 26 | SW10.39 | CGAGCCUUUAGUAAGACUCAUGCCGAGAAAUCGGUCGUGAUGCUGUCGAG |
| 27 | SW10.43 | UUCGUGAGGGCGGUGUGGGAGGCAAGCGGUACGAGCGUACUGUCUGGGCC |

*The 5'-fixed region is missing nucleotide A in the 9th position

TABLE 3

Starting template sequence for SELEX "B".
5'-GGGAAAAGCGAATCATACACAAGA-50N-GCTCCGCCAGAGACCAACCGAGAA-3' (SEQ ID NO:28)
5' PCR primer for SELEX "B":
5'-TAATACGACTCACTATAGGGAAAAGCGAATCATACACAAGA-3' (SEQ ID NO: 29)
3' PCR primer for SELEX "B":
5'-TTCTCGGTTGGTCTCTGGCGGAGC-3' (SEQ ID NO: 30)
Starting sequence of RNA pool for SELEX "B":

TABLE 3-continued

5'-GGGAAAAGCGAAUCAUACACAAGA-50N-GCUCCGCCAGAGACCAACCGAGAA-3' (SEQ ID NO:31)
5' primer for subcloning evolved ligands from SELEX "B":
5'-CGCGGATCCTAATACGACTCACTATAGGGAAAAGCGAATCATACACAAGA-3' (SEQ ID NO: 32)
3' primer for subcloning evolved ligands from SELEX "B":
5'-GGCGAATTCTTCTCGGTTGGTCTCTGGCGGAGC-3' (SEQ ID. NO: 33)

TABLE 4

Evolved gag ligands from SELEX experiment "B"
5'-GGGAAAAGCGAATCATACACAAGA-50N-GCUCCGCCAGAGACCAACCGAGAA-3'
(SEQ ID NO:31)

| Sequence ID no: | Ligand Name | Sequence of randomized region |
|---|---|---|
| 34 | ML8.7 | UGUGAUGGGUGUGUUUUGGUUAGCUGUGGAGGGCCAUGUGGGCUGGACG |
| 35 | ML8.11 | GGUGUGUGUGCGCCGCGAGGUGUCUGAGGAGAGAGGUGGCAGUGGAGGGU |
| 36 | ML8.12 | GGAGGGUGUGCGGACGGGAGCGUGUAGUGAGGCUUUUCAGGCGUUGGACG |
| 37 | ML8.14 | UGUGAUGGGUGUGAUUUUGGUUAGCUGUGGAGGGUUAUGUGGGUCGGACG |
| 38 | ML8.16 | UGUGGGCUUCCUGAGGGGUAGGAACUCUGAAGUCAUGGUUCGUGGUAAGC |
| 39 | ML8.17 | GGAGGGAAUGUGGAAGGGUUUGUGGUGUUUCGCAAAUGCCGCAUGGACGU |
| 40 | ML8.18 | GGGGGGAGAGGCGUGGACGAUGUUUGUGGUUAUGCUGUCGGUUUUGGCUUG |
| 41 | ML8.19 | GGGAUGGAUCGGUGAGACGAGCAGUGGAGUGGUGAGGUGUGGUGUCACGU |
| 42 | ML8.20 | CGUUCGGUGGUGGACAGGGUAAUGUGGAGGGACCGGGUGAUUGUGUAUGU |
| 43 | ML8.21 | UGGAGGGUGGCGGGAGAAGUUUGAGGUCGGGGUCGUAUGAUGUGCGCUAG |
| 44 | ML8.22 | UCACGACGGAGGGCGGAUGAAGGGGGGAAGGUCGUGAGUCCAUGCCGUGU |
| 45 | ML8.23 | GGAUGGGCGUGAAUGGAGGGCAAUGUGUGGGUUUGUUGAGCCAGUUGGU |
| 46 | ML8.24 | ACGGGUCCCUAAGACGUCGUUUCGAGAUGUGUGUUUCGGAAAGAGUAGCG |

TABLE 5

Two point binding data for ligands from gag SELEX "A"

| Ligand | % Ligand bound at 10 nM gag | % Ligand bound at 0.1 nM gag | % Ligand bound at 0.0 nM gag |
|---|---|---|---|
| SW8.1 | 30 | 6.6 | 3.2 |
| SW8.2 | 7.3 | 2.9 | 1.9 |
| SW8.4 | 27 | 2 | 1.3 |
| SW8.6 | 4.1 | 1.7 | 1.5 |
| SW8.20 | 16 | 4.1 | 4.7 |
| SW8.24 | 20 | 4.5 | 2.6 |
| SW8.25 | 11 | 1.1 | 1.0 |
| SW8.27 | 32 | 4.6 | 5.3 |
| SW8.30 | 3.7 | 0.8 | 0.8 |
| SW8.31 | 6.3 | 2.4 | 2.7 |
| SW8.37 | 4.2 | 1.8 | 1.0 |
| SW8.40 | 15 | 8.5 | 3.8 |
| SW10.7 | 8.6 | 3.5 | 3.0 |
| SW10.12 | 11.2 | 0.6 | 0.6 |
| SW10.22 | 33 | 3.1 | 1.7 |
| SW10.25 | 19 | 10 | 13 |
| SW10.28 | 33 | 31 | 16 |
| SW10.34 | 11.8 | 7.9 | 8.2 |
| SW10.39 | 17 | 0.8 | 0.6 |
| SW10.43 | 6.7 | 4.1 | 3.0 |
| Ψ | 87 | 13.4 | 14.7 |
| Round 0 RNA | 3.5 | 4.0 | 6.0 |

We claim:

1. A method for identifying nucleic acid ligands to HIV-1 GAG, comprising:
   a) preparing a candidate mixture of nucleic acids;
   b) contacting the candidate mixture of nucleic acids with HIV-1 GAG, wherein nucleic acids having an increased affinity to HIV-1 GAG relative to the candidate mixture may be partitioned from the remainder of the candidate mixture;
   c) partitioning the increased affinity nucleic acids from the remainder of the candidate mixture; and
   d) amplifying the increased affinity nucleic acids to yield a mixture of nucleic acids enriched for nucleic acids with relatively higher affinity and specificity for binding to HIV-1 GAG, whereby nucleic acids ligands to HIV-1 GAG may be identified.

2. The method of claim 1 further comprising:
   e) repeating steps b), c), and d).

3. The method of claim 1 wherein said candidate mixture of nucleic acids is comprised of single stranded nucleic acids.

4. The method of claim 3 wherein said single stranded nucleic acids are ribonucleic acids.

5. The method of claim 4 wherein said candidate mixture of nucleic acids comprises modified nucleic acids.

6. The method of claim 5 wherein said candidate mixture of nucleic acids comprises 2'-amino (2'-$NH_2$) modified nucleic acids.

7. The method of claim 5 wherein said candidate mixture of nucleic acids comprises 2'-fluoro (2'-F) modified nucleic acids.

8. A nucleic acid ligand to HIV-1 GAG identified according to the method of claim 1.

9. A purified and isolated non-naturally occurring RNA ligand to HIV-1 GAG wherein said ligand is selected from the group consisting of the sequences set forth in SEQ ID NOS. 8–27 and 34–46.

10. A purified and isolated non-naturally occurring nucleic acid ligand to HIV-1 GAG.

* * * * *